US011642070B2

(12) United States Patent
Bannon et al.

(10) Patent No.: US 11,642,070 B2
(45) Date of Patent: May 9, 2023

(54) DIAGNOSTIC SYSTEM AND METHODS FOR SIMULTANEOUSLY DETECTING LIGHT AT MULTIPLE DETECTION LOCATIONS IN A SPECTROSCOPIC SYSTEM

(71) Applicant: Headwall Photonics, Inc., Bolton, MA (US)

(72) Inventors: David Bannon, Hopkinton, MA (US); Domhnull Granquist-Fraser, Acton, MA (US); Paul Bartel, Woburn, MA (US); Kevin Didona, Chelmsford, MA (US); Carson Roberts, Roslindale, MA (US); Blair Simon, Clinton, MA (US)

(73) Assignee: Headwall Photonics, Inc., Bolton, MA (US)

( * ) Notice: Subject to any disclaimer, the term of this patent is extended or adjusted under 35 U.S.C. 154(b) by 1005 days.

(21) Appl. No.: 16/038,551

(22) Filed: Jul. 18, 2018

(65) Prior Publication Data

US 2019/0021646 A1    Jan. 24, 2019

Related U.S. Application Data

(60) Provisional application No. 62/645,621, filed on Mar. 20, 2018, provisional application No. 62/533,865, filed on Jul. 18, 2017.

(51) Int. Cl.
*A61B 5/00* (2006.01)
*A61B 5/1455* (2006.01)

(52) U.S. Cl.
CPC .......... *A61B 5/4064* (2013.01); *A61B 5/0075* (2013.01); *A61B 5/0082* (2013.01);
(Continued)

(58) Field of Classification Search
None
See application file for complete search history.

(56) References Cited

U.S. PATENT DOCUMENTS

| | | | |
|---|---|---|---|
| 2010/0016732 A1* | 1/2010 | Wells | A61B 5/4029 600/476 |
| 2011/0043823 A1* | 2/2011 | Hillmer | G01J 3/36 356/519 |

(Continued)

OTHER PUBLICATIONS

Aanderaa product manual for Oxygen Optode 4330, 4835, 4831 (Year: 2017).*

(Continued)

*Primary Examiner* — Colin T. Sakamoto
(74) *Attorney, Agent, or Firm* — Intrinsic Law Corp.

(57) ABSTRACT

A device and system for non-invasively measuring wavelength-dependent changes in optical absorption of brain tissue damaged by CTE, TBI, concussion, repetitive trauma, and/or Lou Gehrig's disease in comparison to signals from healthy normal tissue for a subject in vivo. The brain, tissues, and fluids superficial to the brain are trans-cranially illuminated by light source(s) in low-absorption spectral windows for tissue in the visible and/or near-infrared parts of the spectrum. Optode(s) are disposed at predetermined radial distance(s) from a light output to collect the scattered and/or deflected signal from the surface of the head. The predetermined radial distance from the light output to the optode is correlated with the depth of tissue penetration for the light collected by the optode. A spectrometer and computer analyze the collected light for characteristic optical signatures of the brain tissue damage utilizing the absorbance and/or reflectance and/or transmission spectra generated as a result.

15 Claims, 11 Drawing Sheets

(52) U.S. Cl.
CPC ...... *A61B 5/14552* (2013.01); *A61B 5/14553* (2013.01); *A61B 5/4088* (2013.01); *A61B 5/6814* (2013.01); *A61B 5/7246* (2013.01); *A61B 5/0042* (2013.01); *A61B 5/0059* (2013.01); *A61B 5/0062* (2013.01); *A61B 5/0073* (2013.01); *A61B 5/1455* (2013.01); *A61B 2562/0233* (2013.01)

(56) References Cited

U.S. PATENT DOCUMENTS

| | | | | |
|---|---|---|---|---|
| 2013/0150726 | A1* | 6/2013 | Riley | A61B 5/02042 600/473 |
| 2013/0225953 | A1* | 8/2013 | Oliviero | A61B 5/4848 600/323 |
| 2015/0011849 | A1* | 1/2015 | Ruchti | A61B 5/14532 600/316 |
| 2015/0011850 | A1* | 1/2015 | Ruchti | A61B 5/6801 600/316 |
| 2015/0015888 | A1* | 1/2015 | Gulati | A61B 5/1455 356/446 |
| 2016/0015316 | A1* | 1/2016 | Borsook | A61B 5/14546 600/340 |
| 2016/0091496 | A1* | 3/2016 | Xu | A61B 5/1455 356/436 |
| 2016/0242682 | A1* | 8/2016 | Gulati | A61B 5/6801 |
| 2016/0249836 | A1* | 9/2016 | Gulati | G01J 3/36 600/316 |
| 2017/0281014 | A1* | 10/2017 | von Luehmann | A61B 5/4064 |
| 2017/0311803 | A1* | 11/2017 | Hirsch | A61B 5/6814 |
| 2019/0159675 | A1* | 5/2019 | Sengupta | A61B 5/14553 |
| 2021/0225194 | A1* | 7/2021 | Pittenger | A61B 5/743 |

OTHER PUBLICATIONS

Biran et al., "Chapter 1 Optrode-Based Fiber Optic Biosensors (Bio-Optrode)" Optical Biosensors: Present and Future, edited by Liglerand Rowe Taitt, ©2002 Elseview Science B.V. (Year: 2002).*

Chin et al., "Chapter 17: Optical Fiber Sensors for Biomedical Applications", Optical-Thermal Response of Laser-Irradiated Tissue, 2nd ed., edited by Welch et al., © Springer Science and Business Media, 2011 (Year: 2011).*

* cited by examiner

| Age | Motor Vehicle Traffic | Falls | Assault | Struck by /Against | Self-Inflicted | All Other Causes |
|---|---|---|---|---|---|---|
| 0-4 | 278 | 37 | 408 | 32 | 0 | 196 |
| 5-14 | 488 | 21 | 131 | 19 | 58 | 158 |
| 15-24 | 3,670 | 139 | 1,515 | 28 | 1,834 | 551 |
| 25-44 | 4,310 | 548 | 2,151 | 88 | 4,587 | 1,186 |
| 45-64 | 3,230 | 2,077 | 1,142 | 126 | 5,601 | 1,710 |
| ≥65 | 1,651 | 9,444 | 357 | 79 | 3,362 | 2,483 |

FIG. 2
(prior art)

DIAGNOSTIC SYSTEM AND METHODS FOR SIMULTANEOUSLY DETECTING LIGHT AT MULTIPLE DETECTION LOCATIONS IN A SPECTROSCOPIC SYSTEM

CROSS-REFERENCE TO RELATED APPLICATIONS

This application claims priority to U.S. Provisional Application No. 62/533,865, titled "Non-Invasive Optical Measurement of Traumatic Brain Injury, Chronic Traumatic Encephalopathy, and Concussions," filed on Jul. 18, 2017, and to U.S. Provisional Application No. 62/645,621, titled "Method for Simultaneously Detecting Light at Multiple Detection Locations in a Spectroscopic System," filed on Mar. 20, 2018, which are hereby incorporated by reference.

TECHNICAL FIELD

This disclosure relates to the detection of neurological damage in the in vivo brain, such as in cases of chronic traumatic encephalopathy (CTE), traumatic brain injury (TBI), concussion, repetitive trauma, Lou Gehrig's disease, Alzheimer's disease, and/or other neurodegenerative conditions.

BACKGROUND

Chronic traumatic encephalopathy (CTE), traumatic brain injury (TBI), concussion, repetitive trauma, and Lou Gehrig's disease cause progressive neurological damage to the brain. For example, the contrast between healthy brain tissue and neurological damage due to advanced CTE disease is shown in FIG. 1. TBI alone killed 53,695 people between 2006 and 2010 in the United States. The breakdown of the TBI causes of these deaths is shown in FIG. 2. All these diseases show similar progressions with onset in the frontal cerebral cortex and then progressing dorsally and inwardly.

One non-invasive method for detection of neurological damage in the brain from CTE, TBI, concussion, repetitive trauma or Lou Gehrig's disease utilizes positron emission tomography (PET). PET scanning uses radioactive tracers, takes on the order of two to four hours per scan, and has a high cost: $3K to $6K per scan (as of 2014). And PET detection of these diseases is still in the research phase. In the case of TBI, prior to this disclosure, there has not been a non-invasive, diagnostic technique for real-time measurement for baseline progression of injury outside of a hospital laboratory or medical setting.

Another non-invasive method for detection of neurological damage in the brain utilizes a spectrographic analysis of light energy scattered and refracted from brain. The light energy is collected separately with a detector that is manually positioned at different distances (e.g., a detector position 1 and then at detector position 2) from the light source, as indicated in FIG. 3. This method introduces errors and inconsistencies in positioning the detector at the same distances from the light source from patient to patient. This method also takes a long time, which increases the likelihood that the patient or technician will move during collection. When the patient or technician moves, the errors and inconsistencies in consistently positioning the detector are compounded.

It would be desirable to overcome the above deficiencies in current technologies. It would also be desirable to have a faster and less expensive method for diagnosing and detecting progressive damage to the brain caused by these neurodegenerative conditions and diseases.

SUMMARY

Example embodiments described herein have innovative features, no single one of which is indispensable or solely responsible for its desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to an apparatus for simultaneously detecting scattered light, deflected light, or a combination thereof from a target in a subject at a plurality of detection locations, the apparatus comprising: a housing; an illumination output disposed on the housing, the illumination output coupled to an illumination source to supply light energy having an illumination wavelength range; a plurality of optodes disposed on the housing, each optode disposed at a predetermined radial distance from the illumination output; and at least one optical fiber coupled to each optode, wherein the number of optical fibers coupled to each optode corresponds to the predetermined radial distance.

In one or more embodiments, the illumination wavelength range comprises 800 nm to 840 nm. In one or more embodiments, the illumination wavelength range consists of 800 nm to 840 nm.

In one or more embodiments, the number of optical fibers coupled to each optode is proportional to the predetermined radial distance such that a lower number of optical fibers are coupled to a first optode disposed at a relatively small radial distance from the illumination output and a higher number of optical fibers are coupled to a second optode disposed at a relatively large radial distance from the illumination output. In one or more embodiments, the number of optical fibers coupled to each optode corresponds to an effective aperture of the respective optode. In one or more embodiments, the higher number of optical fibers coupled to the second optode increases an output signal strength of the second optode.

In one or more embodiments, the plurality of optodes includes a plurality of optode groups, each optode group including two or more optodes, the two or more optodes disposed at a group predetermined radial distance from the illumination output. In one or more embodiments, the plurality of optode groups includes a first optode group disposed at a first group predetermined radial distance from the illumination output, and the first optode group is disposed along a first virtual arc having a first virtual radius from the illumination output equal to the first group predetermined radial distance from the illumination output. In one or more embodiments, the number of optical fibers coupled to each optode in the first optode group corresponds to a respective angular position of the optode on the first virtual arc. In one or more embodiments, the plurality of optode groups includes a second optode group disposed at a second group predetermined radial distance from the illumination output, and the second optode group is disposed along a second virtual arc having a second virtual radius from the illumination output equal to the second group predetermined radial distance from the illumination output. In one or more embodiments, the number of optical fibers coupled to each optode in the second optode group corresponds to a respective angular position of the optode on the second virtual arc.

In one or more embodiments, the target comprises the subject's cerebral spinal fluid.

Another aspect of the invention is directed to a system for simultaneously detecting scattered light, deflected light, or a combination thereof from a target in a subject at a plurality of detection locations, the system comprising: a sensor head comprising: a housing; an illumination output disposed on the housing, the illumination output coupled to an illumination source to supply light energy having an illumination wavelength range; a plurality of optodes disposed on the housing, each optode disposed at a predetermined distance from the illumination source; and at least one optical fiber coupled to each optode, wherein a number of optical fibers coupled to each optode corresponds to the predetermined distance; a plurality of spectrometers, each spectrometer optically coupled to a respective optode via the at least one optical fiber, each spectrometer configured to operate in at least a portion of the illumination wavelength range; a microprocessor-based computer electrically coupled to an optical sensor of each spectrometer.

In one or more embodiments, the computer is programmed to determine if current spectral scan data of the subject has a characteristic spectral signature indicative of neurological damage to or a neurological disease of a brain. In one or more embodiments, the neurological damage or disease includes (a) traumatic brain injury, (b) chronic traumatic encephalopathy, (c) concussion, (d) frontal or temporal cerebral tissue damage, (e) Lou Gehrig's disease, or (f) Alzheimer's disease. In one or more embodiments, data representing the characteristic spectral signature is stored in a memory operably coupled to the computer.

In one or more embodiments, the computer is programmed to compare current spectral scan data of the subject at the target with prior spectral scan data of the target to determine if a change in a spectral property of the target has occurred. In one or more embodiments, the change in the spectral property corresponds to neurological damage to or a neurological disease of a brain. In one or more embodiments, the neurological damage or disease includes (a) traumatic brain injury, (b) chronic traumatic encephalopathy, (c) concussion, (d) frontal or temporal cerebral tissue damage, (e) Lou Gehrig's disease, or (f) Alzheimer's disease.

In one or more embodiments, the computer is programmed to compare the current spectral scan data over a comparison wavelength range with prior spectral scan data over the comparison wavelength range. In one or more embodiments, the comparison wavelength range is 825 nm to 840 nm.

In one or more embodiments, the target comprises the subject's cerebral spinal fluid. In one or more embodiments, the illumination wavelength range comprises 800 nm to 840 nm. In one or more embodiments, the illumination wavelength range consists of 800 nm to 840 nm.

In one or more embodiments, the number of optical fibers coupled to each optode is proportional to the predetermined radial distance such that a lower number of optical fibers are coupled to a first optode disposed at a relatively small radial distance from the illumination output and a higher number of optical fibers are coupled to a second optode disposed at a relatively large radial distance from the illumination output. In one or more embodiments, the number of optical fibers coupled to each optode corresponds to an effective aperture of the respective optode. In one or more embodiments, the higher number of optical fibers coupled to the second optode increases an output signal strength of the second optode.

In one or more embodiments, the plurality of optodes includes a plurality of optode groups, each optode group including two or more optodes, the two or more optodes disposed at a group predetermined radial distance from the illumination output. In one or more embodiments, the plurality of optode groups includes a first optode group disposed at a first group predetermined radial distance from the illumination output, and the first optode group is disposed along a first virtual arc having a first virtual radius from the illumination output equal to the first group predetermined radial distance from the illumination output. In one or more embodiments, the number of optical fibers coupled to each optode in the first optode group corresponds to a respective angular position of the optode on the first virtual arc. In one or more embodiments, the plurality of optode groups includes a second optode group disposed at a second group predetermined radial distance from the illumination output, and the second optode group is disposed along a second virtual arc having a second virtual radius from the illumination output equal to the second group predetermined radial distance from the illumination output. In one or more embodiments, the number of optical fibers coupled to each optode in the second optode group corresponds to a respective angular position of the optode on the second virtual arc.

In another aspect, the invention is directed to a method for simultaneously detecting scattered light, deflected light, or a combination thereof from a target in a subject at a plurality of detection locations, the method comprising placing a sensor head on the subject proximal to the target, the sensor head comprising: a housing; an illumination output disposed on the housing, the illumination output coupled to an illumination source to supply light energy having an illumination wavelength range; a plurality of optodes disposed on the housing, each optode disposed at a predetermined radial distance from the illumination output; and at least one optical fiber coupled to each optode, wherein a number of optical fibers coupled to each optode corresponds to the predetermined radial distance; generating, with the illumination source, the light energy; collecting, with at least one of the optodes, at least one of scattered light and refracted light to provide collected light; and passing at least a portion of the collected light through a spectrometer to determine a spectral profile of the at least a portion of the collected light.

In one or more embodiments, the method further comprises detecting the collected light with an optical sensor, the optical sensor electrically coupled to a computer. In one or more embodiments, the method further comprises determining, with the computer, if current spectral scan data of the subject has a characteristic spectral signature indicative of neurological damage to or a neurological disease of a brain. In one or more embodiments, the neurological damage or disease includes (a) traumatic brain injury, (b) chronic traumatic encephalopathy, (c) concussion, (d) frontal or temporal cerebral tissue damage, (e) Lou Gehrig's disease, or (f) Alzheimer's disease.

In one or more embodiments, the method further comprises comparing, with the computer, current spectral scan data of the subject at the target with prior spectral scan data In one or more embodiments, the change in the spectral property corresponds to neurological damage to or a neurological disease of a brain. In one or more embodiments, the neurological damage or disease includes (a) traumatic brain injury, (b) chronic traumatic encephalopathy, (c) concussion, (d) frontal or temporal cerebral tissue damage, (e) Lou Gehrig's disease, or (f) Alzheimer's disease. In one or more embodiments, the method further comprises comparing, with the computer, the current spectral scan data over a comparison wavelength range with prior spectral scan data over the comparison wavelength range.

BRIEF DESCRIPTION OF THE DRAWINGS

For a fuller understanding of the nature and advantages of the present technology, reference is made to the following detailed description of preferred embodiments and in connection with the accompanying drawings, in which:

FIG. 2 illustrates the causal breakdown of TBI deaths between 2010 and 2016 in the United States according to the prior art;

DETAILED DESCRIPTION

An aspect of the invention relates to a novel apparatus for simultaneously collecting scattered light and/or deflected light at a plurality of detection locations on a subject, such as on the subject's head, resulting in detecting neurodegenerative disease states or traumatic injury. The apparatus includes a housing on which an illumination output and a plurality of optodes (e.g., polished ends of one or more optical fibers) are disposed. One or more optical fibers are optically coupled to each optode to form a signal collection device. The terms "optode" and "light collection unit" can be used alternatively in this application.

Figure 3:
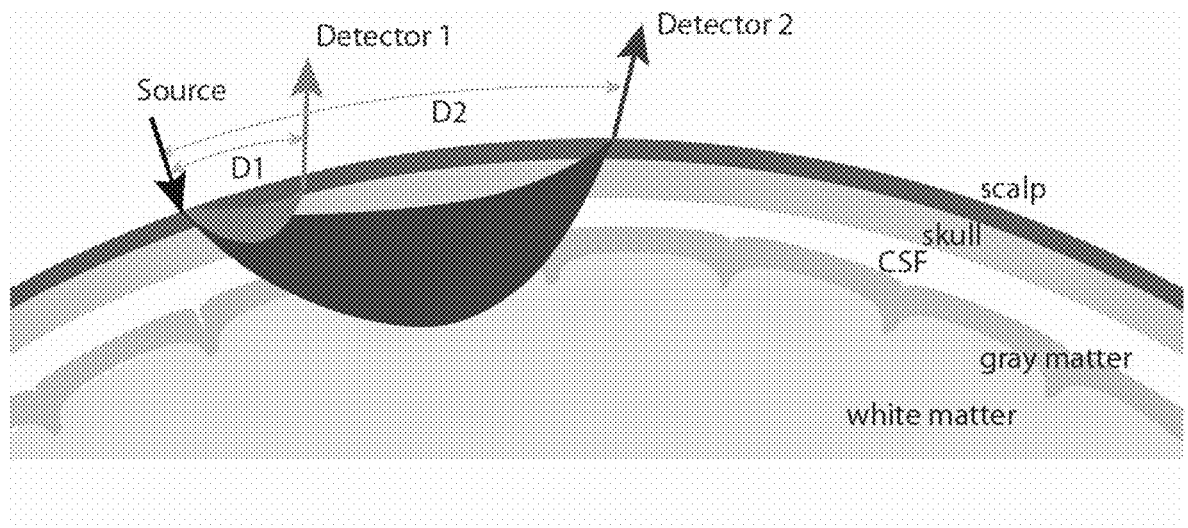
FIG. 3 illustrates multiple detector positions for collecting scattered and/or refracted light according to the prior art.

The optodes are configured and arranged at predetermined and/or fixed radial distances from the light source or light output. The radial distance between the light output and the optodes can correspond to the depth of the tissue sampled (e.g., as illustrated in FIG. 3). The number of optical fibers that are optically coupled to each optode can vary between optodes. For example, optodes located at a closer radial distance from the light source/output can be optically coupled to a lower number of optical fibers while optodes located at a further radial distance from the light source/ output can be optically coupled to a greater number of optical fibers. The additional optical fibers that are optically coupled to the optodes that are located at a further radial distance from the light source/output can compensate or approximately compensate for the attenuation of the scattered light and/or deflected light, which increases with the radial distance from the light source/output.

In operation, light energy passes out of the light output, which is optically coupled to a light source, and is directed to a target surface of a subject's head proximal to an internal target region. At least a portion of the light passes into the internal target region where it is scattered and/or deflected at various angles. The optodes simultaneously collect the scattered and/or deflected light, which passes through respective optical fibers to a spectrometer or a plurality of spectrometers (e.g., a spectrometer for each optode or optode group). A computer is electrically coupled to an optical sensor in the spectrometer(s) to detect its spectrographic output and to analyze the corresponding spectrographic data.

The spectrographic data collected as the back-reflective spectral scatter from the subject's brain and/or surrounding spinal fluid from subjects having neurological damage or disease in the brain is different than spectrographic data from subjects that do not have neurological damage or disease in the brain. The computer can be programmed to analyze the spectrographic data from a subject and determine, using one or more methods, whether the subject may have neurological damage or disease in the brain.

Figure 4:
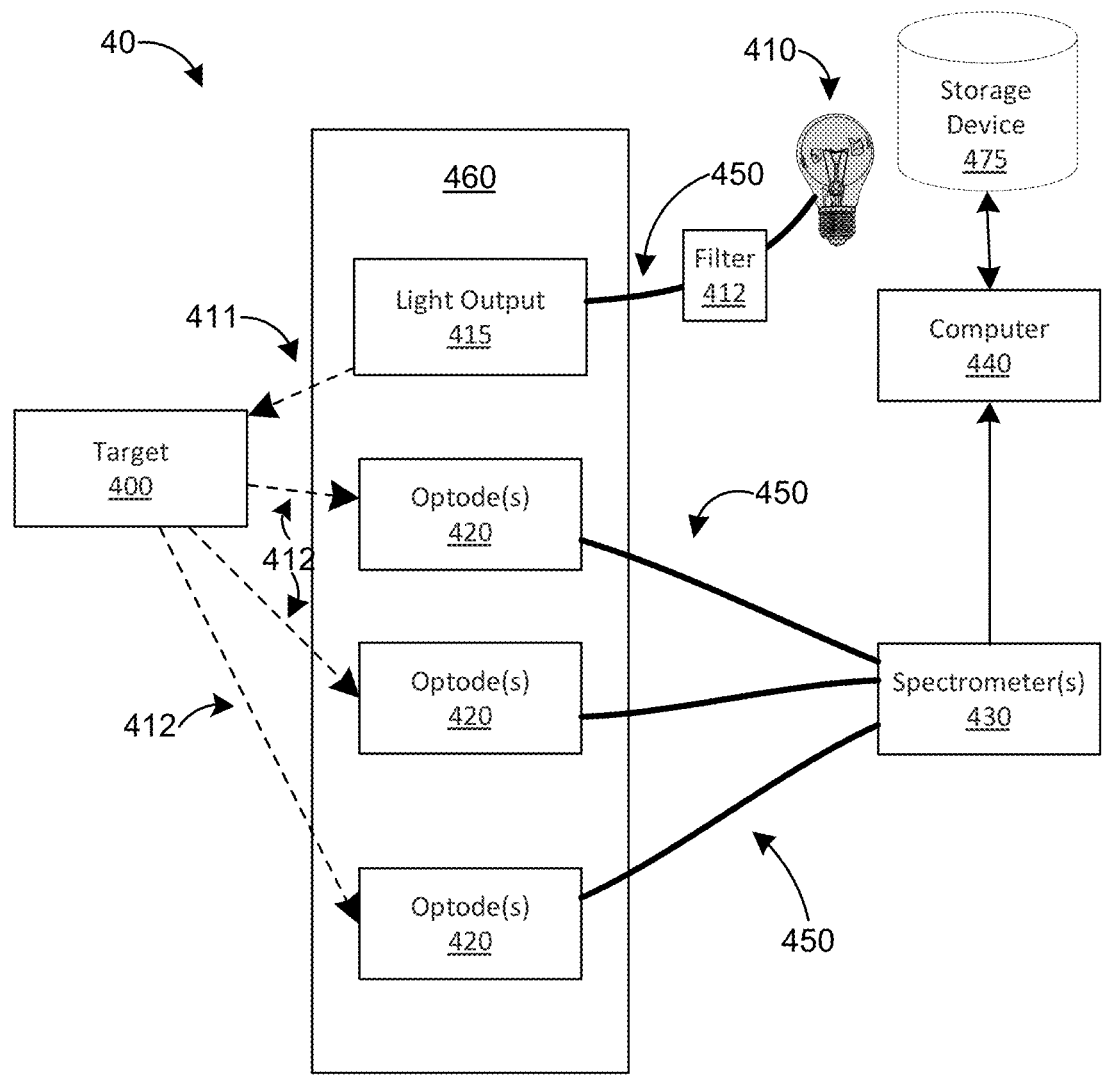
FIG. 4 is a block diagram that illustrates an example of a system 40 for simultaneously detecting scattered light and/or deflected light at multiple detection locations on a subject according to one or more embodiments.

FIG. 4 is a block diagram that illustrates an example of a system 40 for simultaneously detecting scattered light and/or deflected light at multiple detection locations on a subject according to one or more embodiments. The system 40 includes a light or illumination source 410 (in general, light source 410), a light output 415, a plurality of optodes 420, a spectrometer 430, and an optional computer 440.

The light source 410 generates light, which passes through an optional optical fiber and/or light pipe 450 (in general, optical fiber 450) to light output 415 where the light 411 is directed towards a target 400 on an external target surface of a subject. The target 400 can be a region on a human's head proximal to the frontal lobe, the temporal lobe, and/or another region of the human's brain (e.g., in vivo human's brain). The light 411 includes at least some wavelengths that are partially or highly optically transparent such that those wavelengths of light pass through at least a portion of the target 400, for example as discussed below with respect to FIG. 5. For example, at least some light 411 can pass through the scalp and the scull such that it reaches the Cerebral Spinal Fluid (CSF). In another example, at least some light can pass through CSF such that it reaches a portion of the brain matter (which can include gray or white matter), such as the cerebral cortex.

In one example, light source 410 includes one or more light-emitting diodes (LEDs). In another example, light source 410 includes one or more projectors and/or lasers. In another example, light source 410 includes a halogen light source such as a tungsten halogen light source. In one specific example, the tungsten halogen light source can be an HL-2000HP light source available from Ocean Optics, Inc. In some embodiments, light source 510 is optically coupled to one or more optional optical filter(s) 412 (e.g., a bandpass filter) to limit a broadband light source(s) to one or more spectral ranges (e.g., the VIS, NIR-I, and/or NIR-II part of the spectrum). For example, the optical filter(s) 412 can filter the light generated from light source 410 to the spectral wavelength range of about 770 nm to about 850 nm, about 780 nm to about 840 nm, about 790 nm to about 830 nm, about 800 nm to about 820 nm, or any wavelength or wavelength range between any two of the foregoing wavelengths, such that the light exiting the filter only consists of the spectral wavelength range. In a specific example, the optical filter(s) 412 can filter the light generated from light source 410 to the spectral wavelength range of about 800 nm to about 840 nm, such that the light exiting the filter only consists of the spectral wavelength range of about 800 nm to about 840 nm. As used herein, "about" means plus or minus 10% of the relevant value. Light source 410 can emit pulsed light to allow for time of flight (TOF) measurements for the scattered and/or diffracted signal, i.e., introducing measurement separation of charged molecules (ions). In some embodiments, the light output 415 is disposed on the light source 410, for example if the light source 410 includes one or more LEDs. In some embodiments, the light source 410 includes a combination of any of the foregoing.

The light output 415 and optodes 420 are disposed in the housing of a sensor head 460 (e.g., along a common side or edge of the housing). The optodes 420 are disposed at predetermined radial distances from the light output 415. As the light passes through one or more anatomical portions of the human's head (e.g., from dermis through cranium), at least some of the transmitted light scatters, refracts, and/or reflects, and returns to the sensor head 460 where it is collected by one or more optodes 420 (e.g., the polished ends of one or more optical fibers and/or of one or more bundles of optical fibers). Disposing the optodes 420 on the housing of sensor head 460 can allow for repeatable operating conditions since the relative positions of and distances between the sensor head 460 and optodes 420 are fixed in the housing. In some embodiments, the optodes 420 can be adjustably disposed on the housing of sensor head 460 such that one or more of the predetermined radial distances can be adjusted as needed. Adjustably disposing the optodes 420 on the housing of sensor head 460 can allow for different optode 420 configurations within the same scan or between scans. In some embodiments, the light source 410 and the optodes 520 are disposed on repositionable platforms (e.g., via an actuator or other electromechanical mechanism), which can be adjusted by control signals generated by computer 540 or other microprocessor-based controller.

The scattered, refracted, and/or reflected light (in general, collected light 412) collected by optodes 420 is transmitted via optical fibers 450 to one or more spectrometers 430. The optical fibers 450 can be the same optical fibers as the optical fiber bundles that comprise the optodes 420. Alternatively, each optical fiber 450 can be optically coupled to or can include one or more of the optical fiber bundles that comprise each optode 420. In some embodiments, each optode 420 comprises a different number of optical fiber bundles and/or an optical fiber bundle that includes a different number of optical fibers. Each optical fiber and/or optical fiber 450 can have a 50 micron diameter. Alternatively, the number of optical fiber bundles per optode 420 and/or the number of optical fibers per optical fiber bundle is not the same for some of or for each optode 420. In some embodiments, the number of optical fiber bundles per optode 420 and/or the number of optical fibers per optical fiber bundle in each optode 420 can vary with, can depend on, and/or can be proportional to its radial distance from the light output 415. For example, the number of optical fiber bundles per optode 420 and/or the number of optical fibers per optical fiber bundle can increase with (e.g., can be proportional to) the radial distance of the optode 420 from the light output 415. For example, a lower number of optical fibers can be coupled to a first optode 420 disposed at a relatively small radial distance from the light output 415 and a higher number of optical fibers can be coupled to a second optode 420 disposed at a relatively large radial distance from the light output 415. Increasing the number of polished ends and/or the number of optical fibers/optical fiber bundles for a given optode 420 can increase the effective aperture (e.g., collection sensitivity) of the optode 420, which can increase the output signal strength of the optode 420. Increasing the effective aperture of an optode 420 at a relatively large radial distance from the light output 415 can compensate or approximately compensate for the attenuation of the scattered light and/or deflected light collected by the optode 420, the attenuation increasing with the radial distance from the light source/output.

The optical fibers 450 and the optical fibers that comprise the optodes 420 (which can be the same optical fibers in some embodiments) are transmissive in one or more of the spectral ranges discussed herein (e.g., in the VIS, NIR-I, and/or NIR-II part of the spectrum), and can correspond to the wavelengths of the light emitted from the light source 410, to sample the collected light and deliver it to spectrometer(s) 430. In some embodiments, fore optics are attached to the end of the optical fibers 450 (proximal to the respective optode 420) to increase or decrease the numerical aperture of the optodes 420 to optimize signal collection and, therefore, signal-to-noise measurement.

The spectrometer(s) 430 include a diffractive optic consisting of planar, concave, and/or convex diffraction gratings, prisms, and/or optical elements that split the electromagnetic energy of the collected light into its respective wavelengths based on diffraction, refraction, absorption, and reflectance of the electromagnetic energy. This diffractive optic can be either a reflective diffractive optic or a transmission diffractive optic. This diffractive optic can consist of a series of parallel groove structures or it can be an aberration-corrected optic based on an optical profile of a non-parallel series of grooves. In addition to a scalar domain diffractive optic, one embodiment of the technology calls for a resonance domain optical grating to provide very high spectral resolution over a particular spectral bandpass dictated by the spectral signature of the neurodegenerative condition under measurement. The spectrometer(s) 430 can have a concentric, reflective design operating in one or more of the spectral ranges discussed above (e.g., in the VIS, NIR-I, and/or NIR-II, SWIR, or MWIR region of the electromagnetic spectrum) or the spectrometer can have a transmissive design operating with prisms operating in one or more of the spectral ranges discussed above. In some embodiments, the spectrometer(s) 430 can be the same as or similar to the spectrometers described in U.S. Pat. No. 6,266,140, titled "Corrected Concentric Spectrometer," filed on Apr. 29, 1999, U.S. Pat. No. 7,518,722, titled "Multi-Channel, Multi-Spectrum Imaging Spectrometer," filed on Aug. 19, 2005, and/or U.S. Pat. No. 6,839,136, titled "Holographic Grating Spectrum Analyzer," filed on Oct. 19, 2001. Each of the foregoing patents is hereby incorporated by reference. The spectrometer also includes a focal plane array or linear array detector which records the optical signals created to record the resulting spectroscopic scatter. The output(s) of the spectrometer(s) 430 is/are transmitted to an optional microprocessor-based signal and algorithm processing computer 440 for analysis and/or display.

Figure 1:
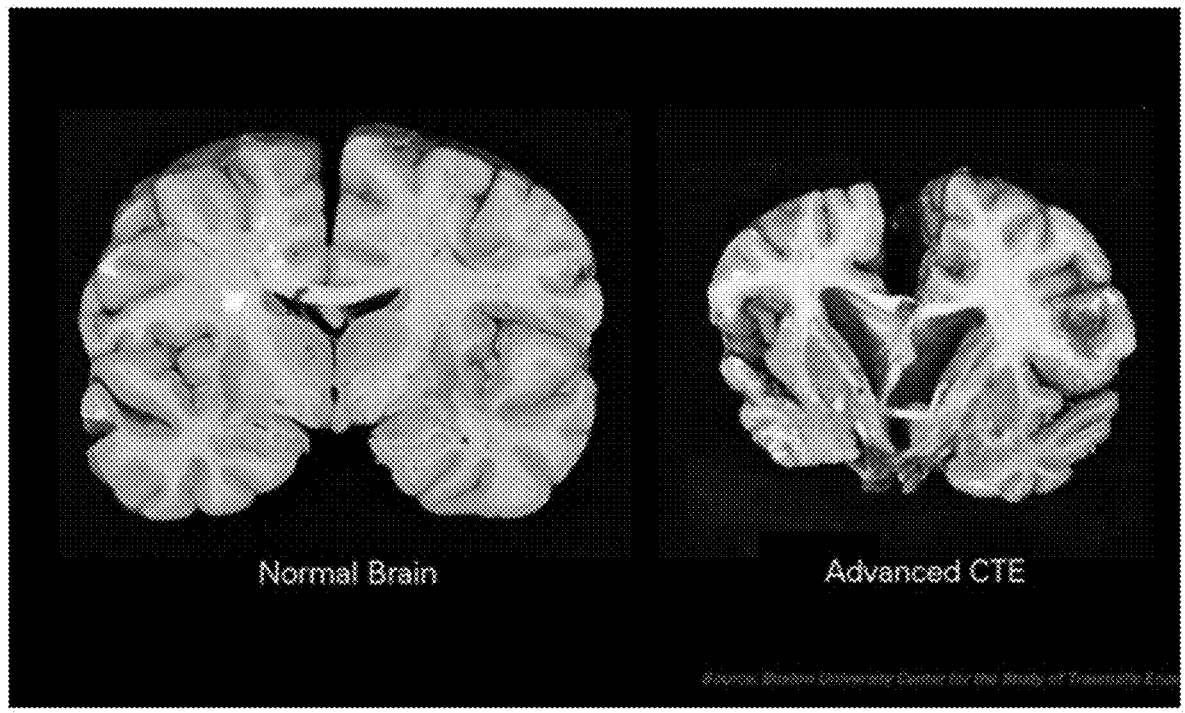
FIG. 1 illustrates the difference between healthy brain tissue and tissue with advanced CTE according to the prior art.

The optional computer 440 is coupled to an optional storage device 475 that can include data relevant to the spectral scan. The computer 440 can be coupled to the storage device 475 via a wired connection or a wireless connection. In addition, the storage device 475 can be disposed locally or remotely from the computer 440. In one example, the storage device 475 includes data from prior spectral scans of the target 400 on the patient. With this information, the computer 440 can include program instructions to compare current spectral scan data with prior spectral scan data to determine if there are any changes in the spectral properties of the target 400 (e.g., in the underlying CSF and/or cerebral cortex, as discussed above), which may indicate neurological damage or disease. In another example, the storage device 475 includes data from prior spectral scans of a first group of individuals with known neurological damage or disease to their brains (e.g., neurological damage due to CTE). The storage device 475 can also include data from prior spectral scans of a second group of individuals that are known to not have neurological damage to their brains (i.e., their brains are normal, e.g., as illustrated in FIG. 1). Alternatively, the second group of individuals can be known to have neurological damage to their brains (i.e., their brains are abnormal, e.g., as illustrated in FIG. 1). The computer 440 can include program instructions to compare the current spectral scan data with data from the first group (i.e., with neurological damage) and/or the second group (i.e., without neurological damage) to determine whether the patient has or appears to have neurological damage. The computer 440 can include program instructions to use statistical analysis, such as multivariate statistical analysis, and derived spectral algorithms to perform the foregoing comparison and analysis.

In another example, the current spectral scan data can have a characteristic spectral signature that may indicate that the individual has (a) TBI, (b) CTE, (c) concussion, (d) frontal and/or temporal cerebral tissue damage resulting from repetitive trauma, (e) Lou Gehrig's disease, (f) Alzheimer's disease, and/or (g) another neurodegenerative condition. The characteristic spectral signature can occur at one or more wavelengths of the spectral scan data. In some embodiments, the computer 440 is programmed with an algorithm or other analytical tools to determine if the current spectral scan data has such a characteristic spectral signature. In some embodiments, the computer 440 can include program instructions to determine if the spectral data includes a characteristic spectral signature without having prior spectral data for the individual. For example, the computer 440 can include program instructions to determine whether the measured spectral intensity (or relative intensity) levels at certain wavelengths correspond to a spectral signature of an individual that may have (a) TBI, (b) CTE, (c) concussion, (d) frontal and/or temporal cerebral tissue damage resulting from repetitive trauma, (e) Lou Gehrig's disease, (f) Alzheimer's disease, and/or (g) another neurodegenerative condition. The computer 440 can include program instructions to compare the current spectral scan data with data from the first or second groups, as discussed above, to determine whether such a characteristic spectral signature is present. In other embodiments, the computer 440 be programmed with an algorithm to determine if a characteristic spectral signature is present without comparing the current spectral scan data to other spectral scan data (i.e., based solely on the absolute or relative spectral intensities and corresponding wavelengths of the current spectral scan data). In another example, the computer 440 includes program instructions to compare the current spectral scan data with prior spectral scan data for the same individual to determine if the individual has any neurological damage or disease, as discussed above. The prior spectral scan data can be stored in the storage device 475. In some embodiments, the computer 440 compares the current spectral scan data with prior spectral scan data for the same individual over a limited wavelength range (e.g., a comparison wavelength range), such as about 825 nm to about 840 nm.

In another aspect, the computer 440 can include program instructions to output a graph or other visual representation (in general, graph) of the current spectral scan data on a display coupled thereto. The computer 440 can also include program instructions to output a graph of prior spectral data from the same individual, which can be overlaid on the same graph as the current spectral scan data. In addition or in the alternative, the computer 440 can include program instructions to output a graph of spectral data from the first group (i.e., with neurological damage) and/or the second group (i.e., without neurological damage), either or both of which can be overlaid on the same graph as the current spectral data. In some embodiments, the computer 440 can include program instructions to visually indicate where the spectral data are different to assist the operator in visually comparing the spectral data. In addition, the computer 440 can include program instructions to output an alarm or other signal if it determines that the current spectral scan data is indicative of neurological damage (e.g., according to the statistical analysis described above). In another aspect, the storage device 475 can include model spectral data generated from a model of hypothetical individuals that have and/or do not have neurological damage. In yet another aspect, the storage device 475 can include data corresponding to characteristic wavelength-dependent spectral signatures of neurological damage to the brain, for example as indicated in the spectral signatures of the CSF and/or brain tissue, and the computer 440 can include program instructions to determine if the current spectral data includes any such characteristic wavelength-dependent spectral signatures.

Figure 5:
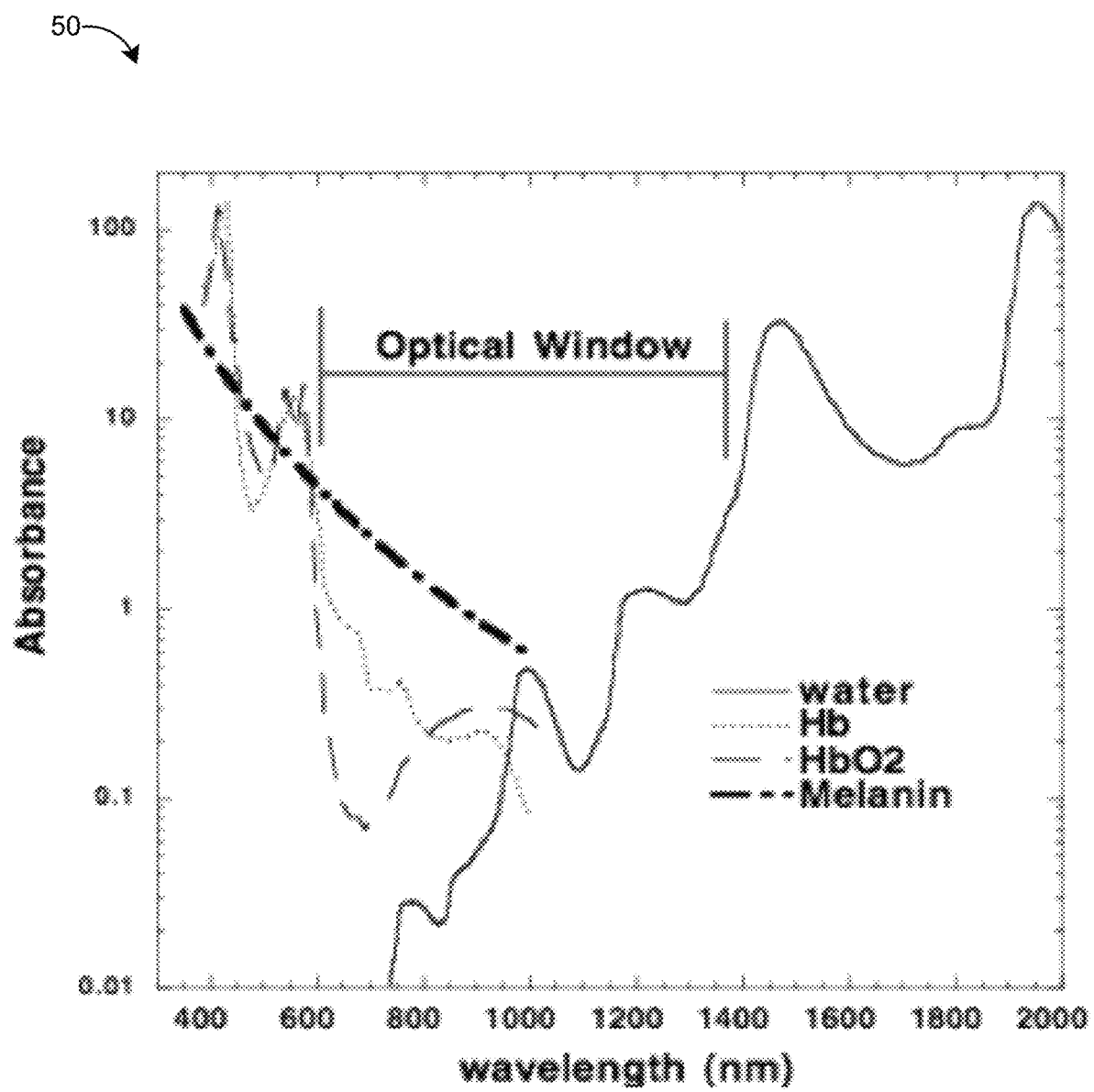
FIG. 5 is a graph 50 of the absorbance of certain bodily components of a mammal as a function of light wavelength.

The system 40 is configured to measure one or more spectral ranges where human tissue and/or anatomy is partially- or highly-optically transparent. FIG. 5 is a graph 50 of the absorbance of certain bodily components of a mammal as a function of light wavelength. Specifically, FIG. 5 illustrates the absorbance of water (H2O), hemoglobin (Hb), oxyhemoglobin (HbO2), and melanin over some or all of the spectrum of 400 nm to 2,000 nm. The wavelengths where absorbance of these bodily components is low (e.g., less than 20) correspond to the spectral ranges where mammalian tissue is partially or highly optically transparent. For example, FIG. 5 illustrates a representative "optical window" where light in the wavelength range of 600 nm to 1,400 nm is partially or highly optically transparent in mammals. Thus, any wavelength or range within this optical window would be partially or highly optically transparent, such as 600 nm to 900 nm, 900 nm to 1,200 nm, 1,200 nm to 1,400 nm, 1,400 nm to 1,700 nm, or any wavelength or range between any two of the foregoing. In some embodiments, the preferred wavelength range is 600 nm to 1,700 nm, which corresponds to the upper end of the visible spectrum (VIS) and the near infrared I spectrum (NIR I). It is noted that wavelengths outside of the representative "optical window" illustrated in FIG. 5 can also be used. For example, an alternate or concurrent range of measurement is in the wavelength range of 1500 nm to 1900 nm, which corresponds to the near infrared II (NIR II) part of the spectrum. Another alternate or concurrent range of measurement is in the wavelength range of 390 nm to 700 nm, which corresponds to the visible part of the spectrum (VIS). In some embodiments, a broad spectrum of light that includes some or all of the foregoing wavelengths can be used. In some embodiments, a broad spectrum of light can be filtered such that only a limited wavelength range is directed to the target, such as the wavelength range of about 770 nm to about 850 nm (or any wavelengths or wavelength ranges therebetween), as discussed above.

Figure 6:
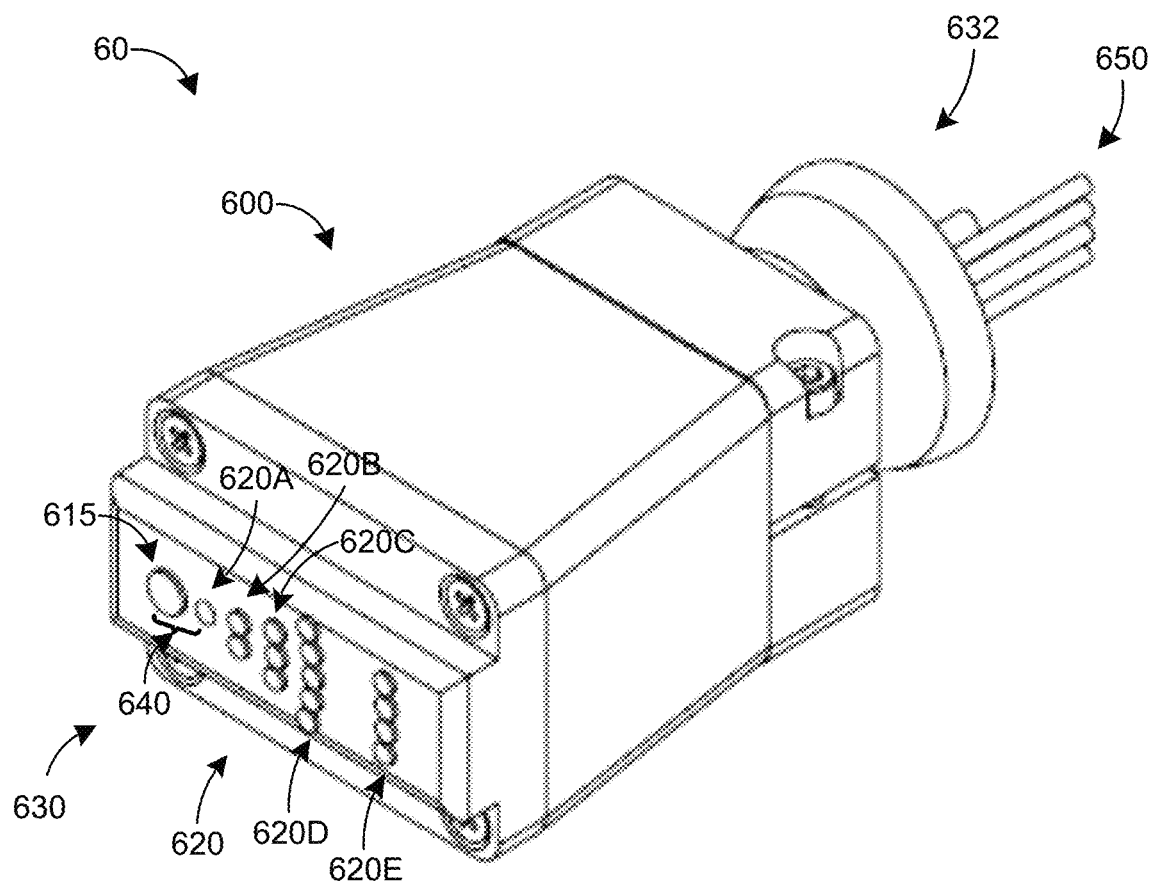
FIG. 6 illustrates a sensor head according to one or more embodiments.

FIG. 6 illustrates a sensor head 60 according to one or more embodiments. Sensor head 60 can be the same as, substantially the same as, or similar to sensor head 460. Sensor head 60 includes a housing 600, a light output 615, an array of optodes 620, and optical fibers and/or light pipes 650 (collectively, optical fibers 650). The light output 615 and optodes 620 are mounted on a proximal end 630 of the housing 600. Thus, the housing 600 sets the spatial geometry and orientation between the light output 615 and the optodes 620.

The optical fibers 650 extend from a distal end 632 of the housing 600. The optical fibers 650 can extend to the optodes 620 and the light output 615. In some embodiments, the optical fibers and/or optical fiber bundles that comprise the optodes 620 can be the same as at least some of or all of the optical fibers 650. As such the optodes 620 can include or can be the polished ends of at least some of or all of the optical fibers 650. Alternatively, the optical fibers and/or optical fiber bundles that comprise the optodes 620 can be optically coupled to at least some of or all of the optical fibers 650. The optical fibers and/or optical fiber bundles that comprise the optodes 620 and/or the optical fibers 650 can have a 50 micron diameter. The optical fibers and/or optical fiber bundles that extend to the light output 615 are optically coupled to a light source (e.g., light source 410).

As discussed above, each optode 620 can include the polished ends of one or more optical fibers and/or one or more optical fiber bundles. The number of polished ends and/or the number of optical fibers/optical fiber bundles can vary between optodes 620. In some embodiments, the number of polished ends and/or the number of optical fibers/optical fiber bundles can vary with, can depend on, and/or can be proportional to the radial distance of the respective optode 620 from the light output 615 and/or the angular position of the respective optode 620 with respect to light output 615, for example as discussed above with respect to optodes 420. Increasing the number of polished ends and/or the number of optical fibers/optical fiber bundles for a given optode 620 can increase the effective aperture (e.g., collection sensitivity) of the optode 620, which can increase the output signal strength of the optode 620. In general, the effective aperture is increased with the radial distance of the optode 620 from the light output 615 to compensate or approximately compensate for attenuation of the scattered light and/or deflected light, which increases with the radial distance from the light source/output.

The light output 615 can be optically coupled to one or more optical fibers 650 to receive light from a light source, such as light source 410 in FIG. 4. In addition or in the alternative, the light output 615 can include a light source (e.g., an LED or a laser) and/or a light source can be disposed in the housing 600, in which case the light source is optically coupled to the light output 615 (e.g., via one or more optical fibers). In some embodiments, a lens, a collimator, or other optics can be disposed on the light output 615 or between the light output 615 and the light source to alter the optical properties of the light that exits the light output 615.

The optodes 620 are disposed at fixed radial distances and angular positions from the light output 615 and from other optodes. As illustrated, the number of optodes 620 varies with the radial distance from light output 615. For example, one optode 620A is located closest to light output 615 at a first radial distance 640 (e.g., 5 mm) or a first group predetermined radial distance from light output 615, followed by a group 620B of two optodes 620 located at a second radial distance (e.g., 10 mm) or a second group predetermined radial distance from light output 615, a group 620C of three optodes 620 located at a third radial distance (e.g., 15 mm) or a third group predetermined radial distance from light output 615, a group 620D of five optodes 620 located at a fourth radial distance (e.g., 20 mm) or a fourth group predetermined radial distance from light output 615, and a group 620E of four optodes 620 located at a fifth radial distance (e.g., 30 mm) or a fifth group predetermined radial distance from light output 615. Thus, the number of optodes 620 in each group 620A-E is not uniform.

In other embodiments, each group 620A-E can have the same number of optodes 620. In yet other embodiments, each group 620A-E can have a different number of optodes 620, though not necessarily following the number of optodes 620 per group 620A-E illustrated in FIG. 6. In addition, other embodiments can include additional or fewer groups 620A-E of optodes 620. Each group 620A-E of optodes 620 can be spaced at regular or irregular distances from the light output 615. Additionally, the optodes 620 within a given group can be spaced at regular or irregular distances from one another and/or angular positions with respect to light output 615. In some embodiments, only a single optode 620 is disposed on the sensor head 600. In some embodiments, the optodes 620 are spaced within a range of 0 to 5 centimeters from the light source 62, which can optimize the sampled depths.

In some embodiments, the sensor head 60 can have more than one light output 615, and each light output 615 can be optically coupled to the same or a different light source. The light outputs can be grouped or clustered together or they can be disposed in different positions on the proximal end 630 of the housing 600. In one example, the light outputs are grouped in virtual columns or virtual arcs, similar to the "vertical" optode groups 620A-E illustrated in FIG. 6. In another example, the illumination sources 62 are disposed laterally along some or all of the length of the proximal end 630 of the housing 600.

The optical fibers 650 optically couple the optodes 620 to one or more spectrometers (e.g., as illustrated in FIG. 4) to deliver the collected light thereto. In some embodiments, each optode 620 is optically coupled to its own spectrometer. Alternatively, two or more optodes can be optically coupled to a common spectrometer. For example, the optode(s) in each optode group 620A-E can be connected to a common spectrometer. In some embodiments, fore optics are attached to the end of the optical fibers 650 (e.g., proximal to the respective optode 620) to increase or decrease the numerical aperture of the optodes 64.

It is noted that FIG. 6 illustrates an exemplary embodiment and one skilled in the art will appreciate that the number of light outputs 615, the number of optodes 620, the number of optical fibers 650, and their respective configuration and arrangement can vary. This figure illustrates an example of one physical pattern and arrangement of the foregoing.

In some embodiments, multiple sensor heads 60 can be used in a given scanning application, where each sensor head 60 is the same, substantially the same, or different than the others. In one example, a plurality of sensor heads 60, each with one or more light outputs 615 and one or more optodes 620, can be placed uniformly or non-uniformly around the surface or a portion of the surface of the scalp. For example, one sensor head 60 can be placed on the subject's left temple and another sensor head 60 can be placed on the subject's right temple.

Figure 7:
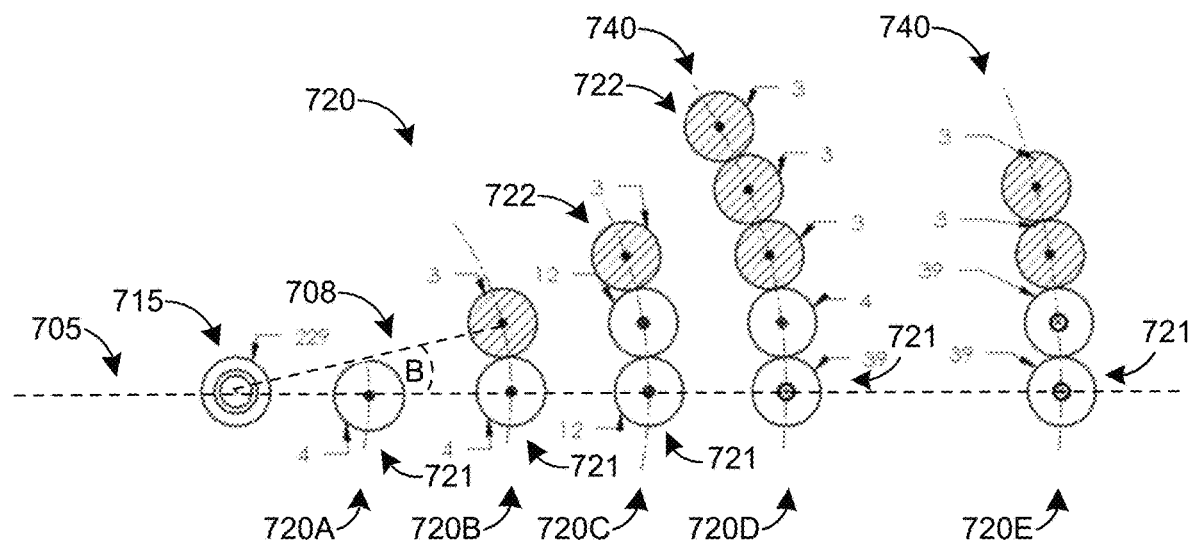
FIG. 7 illustrates an alternative embodiment of the configuration, arrangement, and geometry of a light output and optodes.

FIG. 7 illustrates an alternative embodiment of the configuration, arrangement, and geometry of a light output 715 and optodes 720. In some embodiments, the light output 415, 615 and optodes 420, 620 on respective sensor head 460, 60 can be configured and arranged in the manner illustrated in FIG. 7. In FIG. 7, a reference axis 705 extends from light output 715 through the first optode 721 of each optode group 720A-E. The reference axis 705 extends through the center of light output 715 and through the center of each first optode 721. The angular position of each optode 720 can be defined with respect to reference axis 705. For example, the first optode 721 of each optode group 720A-E has an angular position of 0 or 360 degrees. In another example, the angular position of the second optode 720 in optode group 720B is defined by a line 708 that passes through the center of the light output 715 and through the center of the second optode 720 in optode group 720B. The angle between line 708 and reference line 705 is angle B, which is the angular position of the second optode 720 in optode group 720B. The angular positions of the other optodes 720 are determined in the same way.

The optodes 720 in each optode group 720A-E are disposed adjacent to each other along a virtual arc 740. The virtual arc 740 for a given optode group 720A-E has a virtual radius from light output 715 equal to the radial distance of the optodes 720 from light output 715 in the respective optode group 720A-E. For example, the radial distance of the optodes 720 in optode group 720C is equal to the virtual radius of the virtual arc 740 on which the optodes 720 in optode group 720C are disposed. The radial distance and virtual arc 740 radius of the optode in group 720A can be about 5 mm. The radial distance and virtual arc 740 radius of the optodes in group 720B can be about 10 mm. The radial distance and virtual arc 740 radius of the optodes in group 720C can be about 15 mm. The radial distance and virtual arc 740 radius of the optodes in group 720D can be about 20 mm. The radial distance and virtual arc 740 radius of the optodes in group 720E can be about 30 mm.

An example of the number of optical fiber bundles that can be optically coupled to and/or that comprise the light output 715 and optodes 720 is indicated in FIG. 7. Each optical fiber bundle includes one or more (e.g., a plurality of) optical fibers. Each optical fiber can have a 50 micron diameter. Specifically, FIG. 7 indicates that the light output 715 includes 229 optical fiber bundles. The optode 720 in optode group 720A includes 4 optical fiber bundles. The first optode 721 in optode group 720B includes 4 optical fiber bundles; the second optode 720 in optode group 720B includes 3 optical fiber bundles. The first optode 721 in optode group 720C includes 12 optical fiber bundles. The other optodes 720 in optode group 720C include 12 and 3 optical fiber bundles, respectively, in the upward direction in FIG. 7 (i.e., away from the first optode 721 in optode group 720C). The first optode 721 in optode group 720D includes 39 optical fiber bundles. The other optodes 720 in optode group 720D include 4, 3, 3, and 3 optical fiber bundles, respectively, in the upward direction in FIG. 7 (i.e., away from the first optode 721 in optode group 720D). The first optode 721 in optode group 720E includes 39 optical fiber bundles. The other optodes 720 in optode group 720E include 39, 3, and 3 optical fiber bundles, respectively, in the upward direction in FIG. 7 (i.e., away from the first optode 721 in optode group 720E). Thus, the number of optical fibers or optical fiber bundles coupled to each optode 720 in a given optode group 720A-E can correspond to the angular position of the optode on the corresponding virtual arc of the optode group 720A-E. Those skilled in the art will appreciate that the number, configuration, and/or arrangement of optodes 720, optode groups 720A-E, and fiber optic bundles (e.g., the number of fiber optic bundles that are optically coupled to each optode 720) illustrated in FIG. 7 is provided as a non-limiting example, and that other configurations and/or arrangements are possible.

In some embodiments, the hashed optodes 722 indicate optional optodes 720. A non-functioning spacer optode can be disposed in the location of each hashed optode 722 when the hashed optodes 720 do not comprise optodes 720. In some embodiments, one or more hashed optodes 722 can be a non-functioning spacer optode(s) and one or more hashed optodes 722 can be an optode(s) 720. In some embodiments, spacer optodes are provided to reduce and/or limit crosstalk between adjacent optode groups.

Figure 8:
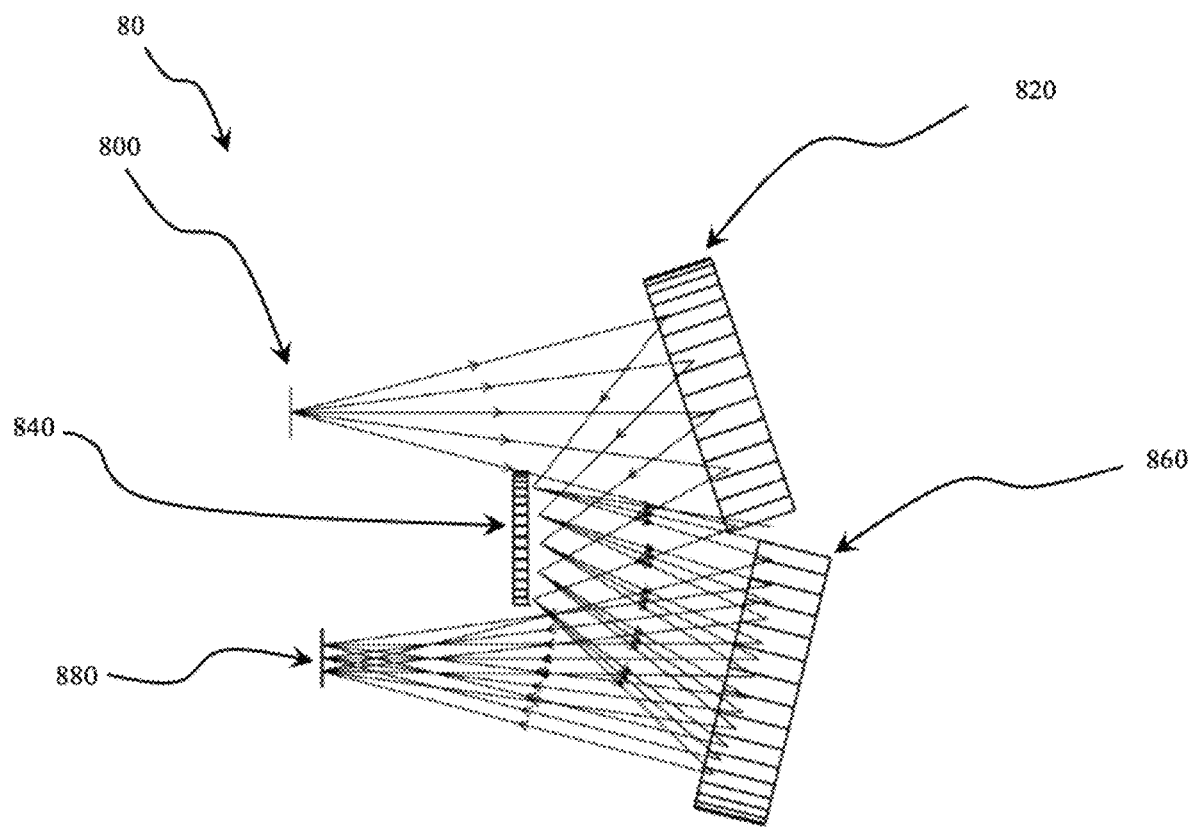
FIG. 8 illustrates an example of a concentric, reflective spectrometer according to one or more embodiments.

FIG. 8 illustrates one example of a concentric, reflective spectrometer 80. The spectrometer 80 includes an entrance slit 800, a concave, concentric collimating mirror 820, a concentric, convex diffraction grating 840, a concentric, concave focusing mirror 860 and an electronic array imaging sensor 880. The spectrometer 80 is configured and arranged to operate in one or more of the spectral ranges described above (e.g., in the UV, VIS, NIR-I, and/or NIR-II part of the spectrum) and corresponding to the wavelengths of light emitted from the illumination/laser excitation source. The imaging sensor 880 can be electrically coupled to a computer (e.g., as illustrated in FIG. 4) to analyze and/or display the spectral content output of spectrometer 80. The spectrometer 80 can be included in any of the embodiments described herein, such as in system 40. The spectrometer can include a range of imaging sensors based on materials comprised of either silicon, InGaAs (Indium-Gallium-Arsenide), or MCT/HgCdTe (mercury cadmium telluride) as determined by the spectral bandpass where the disease state spectral signatures are evident.

An alternative embodiment is a transmissive spectrometer(s) which may include a prism-grating-prism design operating in one or more the spectral ranges described above (e.g., in the UV, VIS, NIR-I, and/or NIR-II part of the spectrum). Another embodiment of a spectrometer(s) includes a concentric catadioptric design operating in one or more the spectral ranges described above (e.g., in the UV, VIS, NIR-I, and/or NIR-II part of the spectrum). In some embodiments, the spectrometer includes an imaging sensor (e.g., imaging sensor 880) that is temporally gated to allow for TOF measurements.

Figure 9:
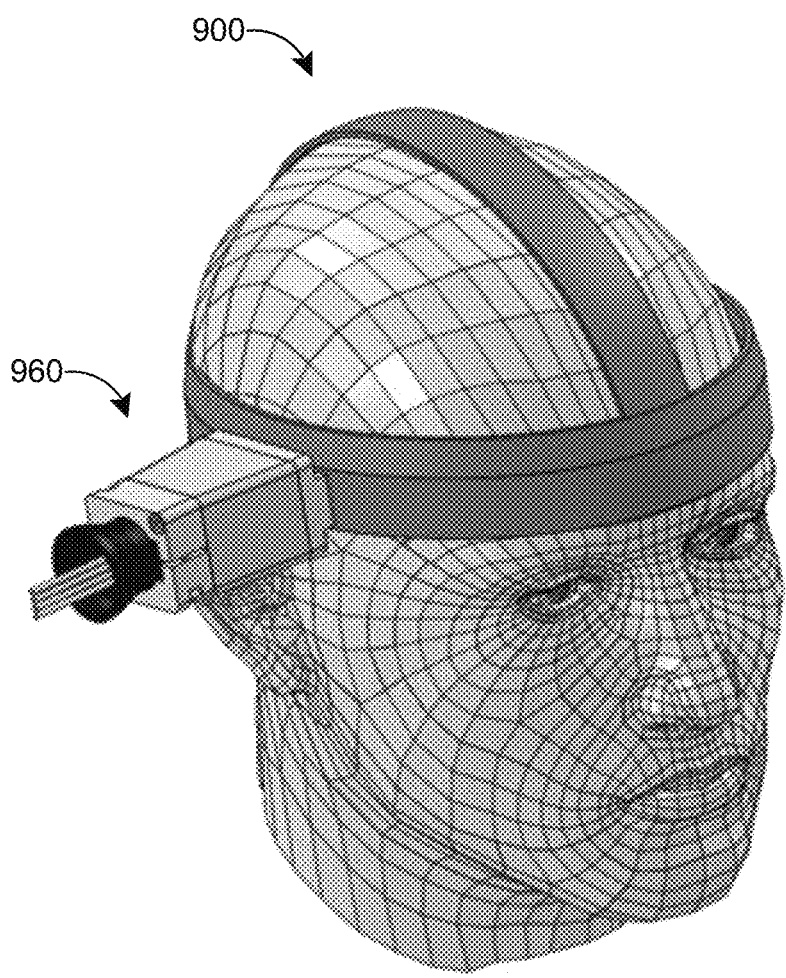
FIG. 9 illustrates an example of a cranial mounting harness for a sensor head.

FIG. 9 illustrates an example of a cranial mounting harness 900 for a sensor head 960. The cranial mounting harness 900 includes a first strap 910 that extends around the circumference of the subject's head and a second strap 920 that extends over the subject's head. Two or more sensor heads can be disposed on the cranial mounting harness 900 in some embodiments. The cranial mounting harness 900 secures the position of the sensor head 960 with respect to the subject's head to reduce or eliminate movement of the sensor head 960 with respect to the subject's head during scanning.

Figure 10:
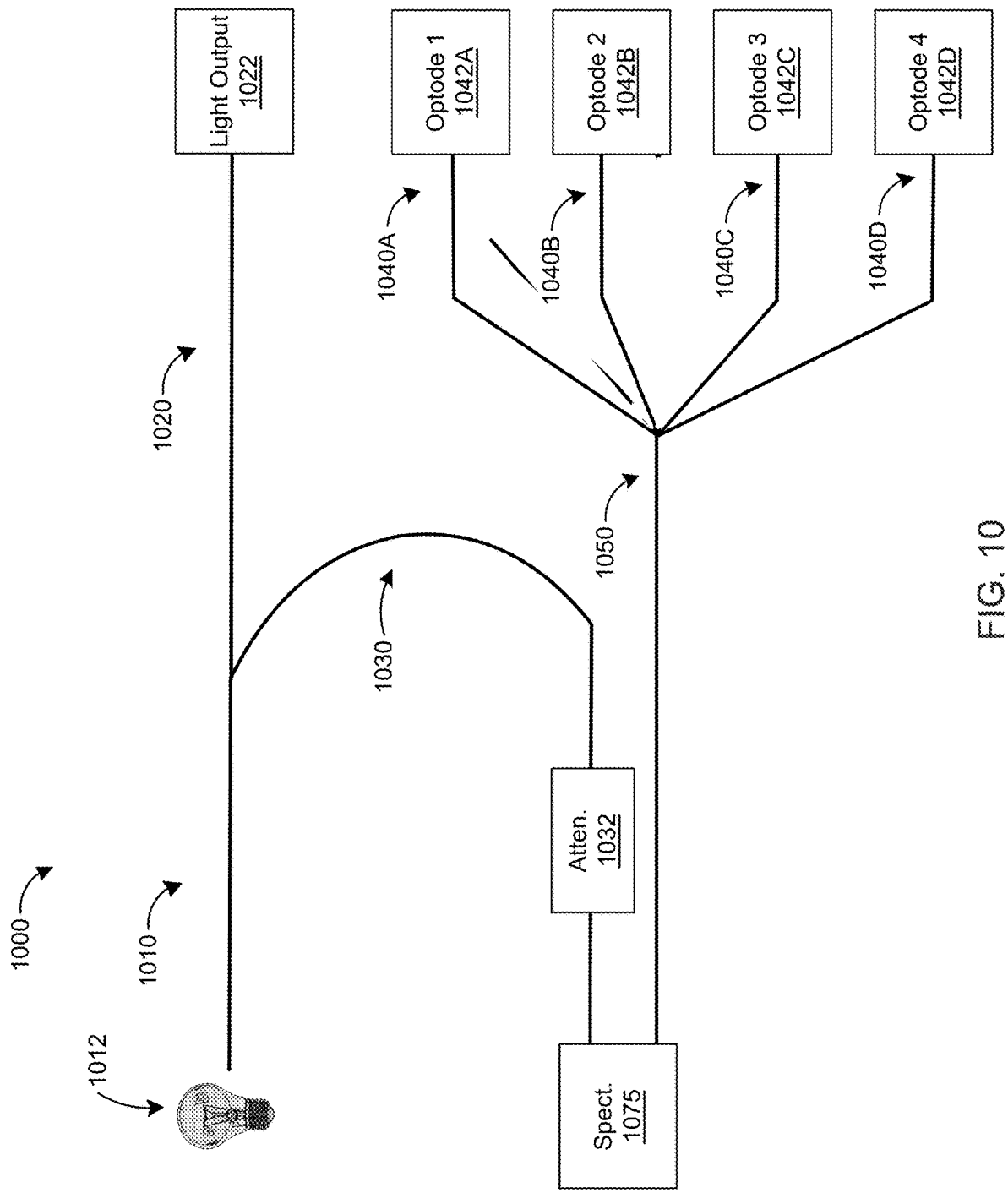
FIG. 10 is a simplified diagram of a fiber optic probe according to one or more embodiments.

FIG. 10 is a simplified diagram of a fiber optic probe 1000 according to one or more embodiments. The probe 1000 can be disposed in the housing (e.g., housing 600) of the sensor head (e.g., sensor head 460, 60) to optically couple (a) the light or illumination source to the light output and (b) the optodes to the spectrometer(s). A first fiber bundle 1010 is optically coupled to light source 1012. Light source 1012 can be the same as or similar to light source 410. The first fiber bundle 1010 includes a plurality of optical fibers, such as 232 optical fibers (e.g., 50 micron optical fibers) in some embodiments. The first fiber bundle 1010 is optically coupled to second and third fiber bundles 1020, 1030. The second fiber bundle 1020 is optically coupled to the first fiber bundle 1010 and to light output 1022. The second fiber bundle 1010 includes a plurality of optical fibers, such as 229 optical fibers (e.g., 50 micron optical fibers) in some embodiments. The third fiber bundle 1030 is optically coupled to the first fiber bundle 1010, to an optical attenuator 1032, and to spectrometer(s) 1075. The third fiber bundle 1010 includes a plurality of optical fibers, such as 3 optical fibers (e.g., 50 micron optical fibers) in some embodiments. The optical attenuator 1032 can attenuate the intensity of a portion of the light emitted from light source 1012 for use as a reference light/signal in the spectrometer(s) 1075. In some embodiments, the optical attenuator 1032 attenuates the light by a factor of 1,000,000 (i.e., 1,000,000:1).

Each optode or optode group 1042A-D is optically coupled to or comprises a respective fourth fiber bundle 1040A-D, similar to the embodiments described herein. For example, each optode or optode group 1042A-D can comprise the polished tips of the optical fibers in the respective fourth fiber bundle 1040A-D. The fourth fiber bundles 1040A-D are optically coupled to a fifth fiber bundle 1050, which is coupled to the spectrometer(s) 1075. In alternative embodiment, each fourth fiber bundle 1040A-D is directly coupled to the spectrometer(s) 1075. In some embodiments, each fourth fiber bundle 1040A-D is directly coupled to a corresponding spectrometer 1075 such that each fourth fiber bundle 1040A-D and each optode or optode group 1042A-D has a dedicated spectrometer 1075. Each fourth fiber bundle 1040A-D includes one or a plurality of optical fibers (e.g., 50 micron optical fibers) and/or one or a plurality of optical fiber bundles (e.g., as discussed above). In some embodiments, each fourth fiber bundle 1040A-D includes 3-39 optical fibers (e.g., 3, 4, 12, and/or 39 optical fibers) and/or 3-39 optical fiber bundles (e.g., 3, 4, 12, and/or 39 optical fiber bundles). In some embodiments, at least one of the fourth fiber bundles 1040A-D is optically coupled to an inactive optode or optode group (e.g., a spacer), such as fiber bundle 1040A and optode or optode group 1040A in some embodiments. The fourth fiber bundles 1040A-D can include additional or fewer optical fiber bundles which can be optically coupled to a corresponding additional or fewer optodes. In some embodiments, the fourth fiber bundles 1040A-D include up to 14 fiber bundles (e.g., bundles 1040A-M (not illustrated)) that are optically coupled to up to 14 optodes or optode groups (e.g., optodes or optode groups 1042A-M (not illustrated)). As discussed above, some of the fiber bundles can be optically coupled to inactive or spacer optodes or optode groups.

Figure 11:
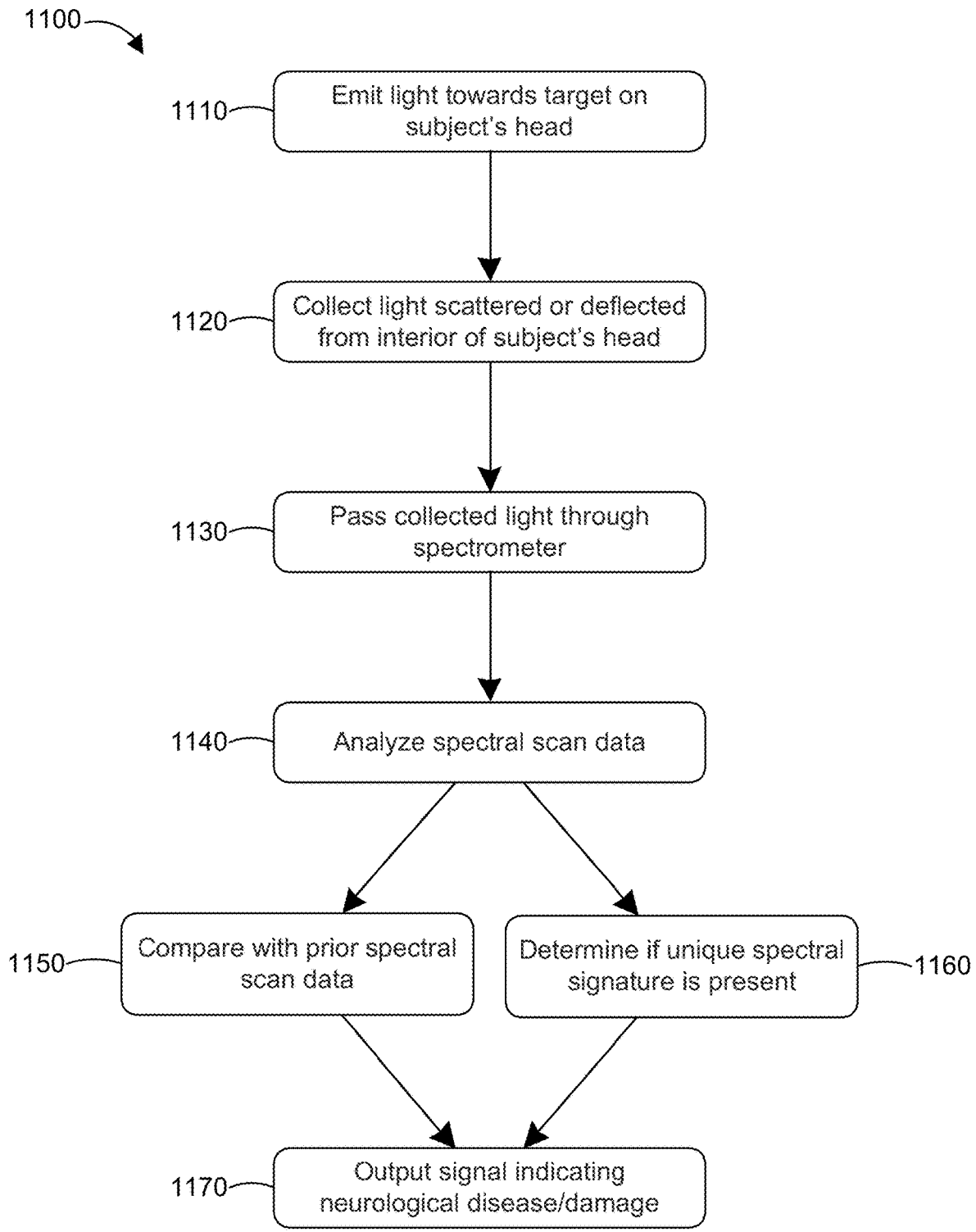
FIG. 11 is a flow chart for a method for determining the spectral signature of the tissue and/or associated fluids within the cranial cavity.

FIG. 11 is a flow chart 1100 for a method for determining the spectral signature of the tissue and/or associated fluids within the cranial cavity. In step 1110, light is emitted from a light source (e.g., a broad spectrum halogen light source) towards a target on a subject's head, for example as discussed above. The light source can be included in and/or can be optically coupled to a light output on one or more sensor heads, such as sensor head 460 and/or 60. The light source emits light having at least some wavelengths that are partially- or highly-optically transparent (e.g., as discussed above) to the target such that those wavelengths of light pass through at least a portion of the target and into the interior region of the subject's head. The light emitted from the light source can pass through one or more filters (e.g., a bandpass filter) to limit the wavelength range of light directed to the target. The interior region of the subject's head can include the CSF and/or the cerebral cortex.

In step 1120, the light scattered, refracted, and/or deflected from the interior region of the subject's head is collected. The scattered, refracted, and/or deflected light can be collected with one or more optodes (e.g. optodes 420, 620, and/or 720). The optodes can be disposed at predetermined radial distances and/or angular positions from the light source or light output, for example in a sensor head as described above.

In step 1130, the collected light is passed through one or more spectrometers (e.g., spectrometer(s) 430 and/or spectrometer 60) via optical fibers and/or light pipes that extend from the optodes to the spectrometer(s). The spectrometer(s) is/are configured and arranged to operate in one or more of the spectral ranges described above (e.g., in the UV, VIS, NIR-I, and/or NIR-II part of the spectrum), and corresponding to the wavelengths of light emitted from the light source and/or the wavelength range that passes through the optional filter.

In step 1140, the spectral scan data is analyzed, for example by a computer coupled to the output of the spectrometer. The computer can include computer-readable instructions, which can include one or more algorithms, to analyze and/or process the spectral scan data. In some embodiments, the computer compares 1150 the current spectral scan data with prior spectral scan data. The computer can compare the current spectral scan data with prior spectral scan data from the same subject. In some embodiments, the computer compares the current spectral scan data with prior spectral scan data for the same individual over a limited wavelength range (e.g., a comparison wavelength range), such as about 825 nm to about 840 nm. The computer can also output a graph of the current spectral scan data on a display coupled thereto. The computer can also output a graph of prior spectral data from the same individual, which can be overlaid on the same graph as the current spectral scan data. The overlay can allow a user to determine visually whether there any changes in the spectral scan data between the current spectral scan data and the prior spectral scan data. Such changes can correspond to neurological damage or disease, for example as a result of (a) TBI, (b) CTE, (c) concussion, (d) frontal and/or temporal cerebral tissue damage resulting from repetitive trauma, and/or (e) Lou Gehrig's disease.

In addition or in the alternative, the computer can compare 1150 the current spectral scan data with prior spectral scan data from a group of individuals known to have or not have neurological damage or disease. In some embodiments, the computer compares the current spectral scan data with prior spectral scan data from a group of individuals over a limited wavelength range (e.g., a comparison wavelength range), such as about 825 nm to about 840 nm.

In some embodiments, the computer determines 1160 if a characteristic spectral signature is present in the current spectral scan data that may indicate that the individual has neurological damage or disease, for example as a result of (a) TBI, (b) CTE, (c) concussion, (d) frontal and/or temporal cerebral tissue damage resulting from repetitive trauma, and/or (e) Lou Gehrig's disease. The characteristic spectral signature can occur at one or more wavelengths of the spectral scan data, as discussed herein. In some embodiments, a characteristic spectral signature can occur in the wavelength range of 825 nm to 840 nm. The characteristic spectral signature can occur at or can be a function of the radial distance of the optode(s) that collect the scattered, refracted, and/or deflected light. For example, the spectra of the collected light may be different at first and second radial distances. Moreover, the difference in the spectra (e.g., difference in intensities or relative intensities such as normalized intensities) between first and second radial distances can be different between a healthy subject and a subject that has neurological damage or disease. Thus, the difference in the spectral intensities between first and second radial distances can be a spectral signature that can indicate whether the subject has neurological damage or disease.

In a specific example, the difference in the spectral intensities in the spectral range of 825 nm to 840 nm and at radial distances of 15 mm and 20 mm can indicate whether the subject has neurological damage or disease. In some embodiments, non-spectral variables (e.g., subject's age) combined with the spectral intensities, difference in spectral intensities, and/or radial distance of the collected light can indicate whether the subject has neurological damage or disease. For example, the spectral intensities and/or difference in spectral intensities can be normalized with respect to the subject's age, and the normalized spectral intensities and/or normalized difference in spectral intensities can indicate whether the subject has neurological damage or disease. In some embodiments, spectral angle mapping can be applied to the spectral intensity data. In one example, a first variate (V1) can be created by calculating the area between a first graph of the spectral intensity at a first radial distance over a predetermined wavelength range and a second graph of the spectral intensity at a second radial distance over the predetermined wavelength range. In a specific example, the predetermined wavelength range can be about 825 nm to about 840 nm and/or the first and second radial distances can be 15 mm and 20 mm, respectively. One skilled in the art will appreciate that other wavelength ranges and/or other radial distances, and combinations thereof, can be used to create the first variate. A second variate (V2) can be based the patient's age, or a normalization of the patient's age, at the time of scanning/data collection. A plot of V1 vs. V2 can indicate whether a person or group has neurological damage or disease. In some embodiments, the left- and right-side of the patient's skull can be scanned, and the spectral intensity data can be averaged, e.g., across the predetermined wavelength range, to calculate V1.

In some embodiments, the computer compares 1150 the current spectral scan data with prior spectral scan data from the same subject to determine 1160 if a characteristic spectral signature is present in the current spectral scan data. In other embodiments, the computer compares 1150 the current spectral scan data with prior spectral scan data from the same subject or it can determine 1160 if a characteristic spectral signature is present in the current spectral scan data.

In step 1170, the computer outputs a signal that indicates that the individual has (or does not have) neurological damage or disease (e.g., based on the comparison 1150 and/or the determination 1160). The signal can be an alarm (e.g., an audible and/or visual alarm), a notification, or other signal.

The embodiments described and illustrated herein are not meant by way of limitation and are rather exemplary of the kinds of features and techniques that those skilled in the art might benefit from in implementing a wide variety of useful products and processes. For example, in addition to the applications described in the embodiments above, those skilled in the art would appreciate that the present disclosure can be applied to other applications.

This disclosure should not be considered limited to the particular embodiments described above, but rather should be understood to cover all aspects of the invention as set forth herein. Various modifications, equivalent processes and spectral processing algorithms, as well as numerous structures to which embodiments of the invention may be applicable, will be readily apparent to those skilled in the art to which the invention is directed upon review of this disclosure.

What is claimed is:

1. A system for simultaneously detecting scattered light, deflected light, or a combination thereof from a target in a subject at a plurality of detection locations, the system comprising:
    a sensor head comprising:
        a housing;
        an illumination output disposed on the housing, the illumination output coupled to an illumination source to supply light energy having an illumination wavelength range;
        a plurality of light collection units disposed on the housing, each light collection unit comprising one or more polished ends of one or more respective optical fibers, each light collection unit disposed at a respective predetermined radial distance from the illumination output,
        wherein a number of the polished ends in each light collection unit corresponds to the respective predetermined distance;
    a plurality of spectrometers, each spectrometer optically coupled to a respective light collection unit via the respective optical fiber(s), each spectrometer configured to operate in at least a portion of the illumination wavelength range; and
    a microprocessor-based computer electrically coupled to an optical sensor of each spectrometer.

2. The system of claim 1, wherein the computer is programmed to determine if current spectral scan data of the subject has a characteristic spectral signature indicative of neurological damage to or a neurological disease of a brain.

3. The system of claim 2, wherein the neurological damage or disease includes (a) traumatic brain injury, (b) chronic traumatic encephalopathy, (c) concussion, (d) frontal or temporal cerebral tissue damage, (e) Lou Gehrig's disease, or (f) Alzheimer's disease.

4. The system of claim 2, wherein data representing the characteristic spectral signature is stored in a memory operably coupled to the computer.

5. The system of claim 1, wherein the computer is programmed to compare current spectral scan data of the subject at the target with prior spectral scan data of the target to determine if a change in a spectral property of the target has occurred.

6. The system of claim 5, wherein the change in the spectral property corresponds to neurological damage to or a neurological disease of a brain.

7. The system of claim 6, wherein the neurological damage or disease includes (a) traumatic brain injury, (b) chronic traumatic encephalopathy, (c) concussion, (d) frontal or temporal cerebral tissue damage, (e) Lou Gehrig's disease, or (f) Alzheimer's disease.

8. The system of claim 5, wherein the computer is programmed to compare the current spectral scan data over a comparison wavelength range with prior spectral scan data over the comparison wavelength range.

9. The system of claim 5, wherein the comparison wavelength range is 825 nm to 840 nm.

10. The system of claim 1, wherein the target comprises the subject's cerebral spinal fluid.

11. The system of claim 1, wherein the illumination wavelength range comprises 800 nm to 840 nm.

12. The system of claim 11, wherein the illumination wavelength range consists of 800 nm to 840 nm.

13. The system of claim 1, wherein the number of polished ends in each light collection unit is proportional to the respective predetermined radial distance such that a lower number of polished ends are in a proximal light collection unit disposed at a relatively small radial distance from the illumination output and a higher number of polished ends are in a distal light collection unit disposed at a relatively large radial distance from the illumination output.

14. The system of claim 13, wherein the number of polished ends in each light collection unit corresponds to an effective aperture of the respective light collection unit.

15. The system of claim 13, wherein the higher number of polished ends in the distal light collection unit increases an output signal strength of thedistal light collection unit.

* * * * *